United States Patent [19]
Carney et al.

[11] 4,207,415
[45] Jun. 10, 1980

[54] METHOD OF PRODUCING 2-DEOXYFORTIMICIN A

[75] Inventors: Ronald E. Carney, Gurnee; Jerry R. Martin, Waukegan; James B. McAlpine, Libertyville; John S. Tadanier, Waukegan, all of Ill.

[73] Assignee: Abbott Laboratories, North Chicago, Ill.

[21] Appl. No.: 9,637

[22] Filed: Feb. 5, 1979

[51] Int. Cl.$^2$ ............................................. C07H 15/22
[52] U.S. Cl. ........................ 536/17 R; 260/345.7 R; 548/336
[58] Field of Search ........................ 260/345.7; 536/17

[56] References Cited

U.S. PATENT DOCUMENTS

| 4,078,139 | 3/1978 | Barton et al. | 536/17 |
| 4,091,032 | 5/1978 | Tadanier et al. | 260/345.7 |

Primary Examiner—Howard T. Mars
Assistant Examiner—G. T. Breitenstein
Attorney, Agent, or Firm—Robert L. Niblack; Gildo E. Fato; Joyce R. Niblack

[57] ABSTRACT

An improved method for producing the antibiotic 2-deoxyfortimicin A, the method comprising the process of producing said antibiotic directly from fortimicin A in a four step process which results in a 50-60 percent yield of product.

8 Claims, No Drawings

METHOD OF PRODUCING 2-DEOXYFORTIMICIN A

BACKGROUND OF THE INVENTION

2-Deoxyfortimicin A is a novel aminoglycoside antibiotic disclosed in commonly assigned U.S. patent application Ser. No. 863,006, filed Dec. 21, 1977. The antibiotic has the following structure:

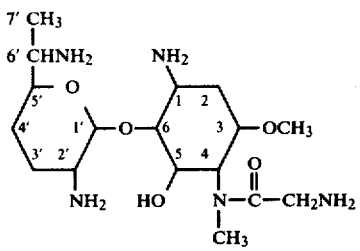

2-Deoxyfortimicin A has in vitro anti-bacterial activity equal to that of fortimicin A, but enhanced in vivo activity against certain bacteria such as *Klebsiella pneumoniae* and *Proteus mirabilis*. Furthermore, 2-deoxyfortimicin A could not be inactivated by R-factor carrying microorganisms which might modify the 2-hydroxyl group of the parent fortimicins.

Production of 2-deoxyfortimicin A heretofore has required a lengthly process which resulted in only a 25–30% yield of the antibiotic. The method involved producing 2-deoxyfortimicin A from fortimicin B, having all primary amino groups protected by benzyloxycarbonyl groups and the $C_5$ hydroxyl and $C_4$ secondary amino group blocked by a suitable aldehyde to form an oxazolidine ring, which, upon treatment with a hydrocarbonsulfonyl halide or anhydride, is converted to a 2-O-hydrocarbonsulfonyl ester, such as a 2-O-methanesulfonyl ester.

The ester in turn is converted to a 1,2',6'-tri-N-benzyloxycarbonyl-2-O-hydrocarbonsulfonyl ester derivative, which, following acid hydrolysis of the oxazolidine ring, is N-deblocked by catalytic hydrogenolysis in the presence of an acid. When the resulting 2-O-hydrocarbonsulfonylfortimicin B salt is converted to the free base, the intermediate, 1,2-epiminofortimicin B is obtained. Continuing the process, catalytic hydrogenolysis of 1,2-epiminofortimicin B gives 2-deoxyfortimicin B which in turn is converted to the 1,2',6'-tri-N-benzyloxycarbonyl intermediate by treatment with a suitable acylating agent such as N-(benzyloxycarbonyloxy)succinimide. The tri-N-benzyloxycarbonyl intermediate is acylated with an activated carboxylic acid derivative to obtain a per-N-blocked 2-deoxy-4-N-acylfortimicin B derivative which is converted to tetra-N-benzyloxy-2-deoxyfortimicin A by reacting the fortimicin B intermediate with an active ester such as the N-hydroxysuccinimide ester of N-benzyloxycarbonylglycine in the presence of tetrahydrofuran. Chromatography yields the per-N-blocked intermediate which is converted to 2-deoxyfortimicin A as the tetrahydrochloride salt by hydrogenolysis in methanolic hydrogen chloride in the presence of 5% palladium on carbon.

The yield generally obtained from the above-described procedure is about 25–30 percent and requires separation of 2-deoxyfortimicin A from a co-produced end product. There has been a need for a simpler, more economical, higher yield processes for producing this valuable antibiotic. The present invention provides such a process which requires fewer steps and results in a 50–60 percent yield of 2-deoxyfortimicin A.

SUMMARY OF THE INVENTION

The present invention provides a four-step process of producing 2-deoxyfortimicin A directly from fortimicin A. Generally speaking, the process of the present invention involves converting fortimicin A to a per-N-blocked fortimicin A intermediate, having all primary amino groups blocked by, for example, benzyloxycarbonyl groups which is accomplished by treating the base with an activated carboxylic acid derivative such as the benzyloxycarbonyl ester of N-hydroxysuccinimide. The resulting per-N-blocked fortimicin A intermediate is converted to a tetra-N-benzyloxycarbonylfortimicin A-2-O-thiocarbonylimidazolide by reaction with N,N'-thiocarbonyldiimidazole which is in turn converted to 2-deoxy-tetra-N-benzyloxycarbonylfortimicin A by treatment with tri-n-butyl stannane in dioxane. Catalytic hydrogenolysis in the presence of 5% palladium over carbon yields the desired product.

DETAILED DESCRIPTION OF PREFERRED EMBODIMENTS

The following examples further illustrate the process of this invention.

EXAMPLE I

Tetra-N-benzyloxycarbonylfortimicin A

Fortimicin A sulfate (2.5 g) was dissolved in water (20 ml) and applied to a column of Dowex 1×2 (OH⁻) resin (Dow Chemical) on a column 1.7 ×15 cm. The basic percolate was collected and lyophilized to give 1.51 g of the free base. The free base, fortimicin A (1.51 g, 3.74 mmole) was dissolved in a mixture of water (19 ml) and methanol (39 ml), the solution was cooled in an ice bath with stirring and treated with the benzyloxycarbonyl ester of N-hydroxysuccinimide (3.8 g, 15.2 mmole). The mixture was allowed to stand at room temperature overnight. Solvent was removed and the crude residue was chromatographed over silica gel to afford 2.25 g of tetra-N-benzyloxycarbonylfortimicin A. The carbon magnetic resonance spectrum is set forth in the Table following the Examples.

EXAMPLE II

Tetra-N-benzyloxycarbonylfortimicin A-2-O-thiocarbonylimidazolide

Tetra-N-benzyloxycarbonylfortimicin A (2.5 g, 2.65 mmole) and N,N'-thiocarbonyldiimidazole (1.0 g, 5.6 mmole) were dissolved in ethylacetate (40 ml) and heated under reflux for 7½ hours. Solvent was removed and the residue chromatographed over silica gel in ethylacetate-isooctane (7:3 v/v) to give 1.9 g of tetra-N-benzyloxycarbonylfortimicin A-2-O-thiocarbonyl imidazolide. The carbon magnetic resonance spectrum of the compound of this Example is set forth in the Table following the Examples.

EXAMPLE III

2-Deoxy-tetra-N-benzyloxycarbonylfortimicin A

A solution of tetra-N-benzyloxycarbonyl-2-O-thiocarbonyl imidazolide (200 mg, 0.19 mmole) in dioxane (20 ml) was added dropwise to a solution of tri-N-butyl stannane (0.2 ml) in dioxane (20 ml). The mixture was heated under reflux in an atmosphere of nitrogen for three hours, and the solvent removed. Chromatography of the residue over a column of silica gel afforded 144 mg of 2-deoxy-tetra-N-benzyloxycarbonylfortimicin A whose carbon magnetic resonance spectrum is set forth in the Table following the examples.

EXAMPLE IV

2-Deoxyfortimicin A hydrochloride

2-Deoxy-tetra-N-benzyloxycarbonylfortimicin A (144 mg, 0.155 mmole) was dissolved in methanolic hydrochloric acid (25 ml, 0.064 N) and hydrogenated over 5% Pd-C (120 mg) at three atmospheres for four hours. The catalyst was removed by filtration and solvent removed from the filtrate to yield 86 mg of 2-deoxyfortimicin A hydrochloride.

The free base is readily obtainable by methods well known in the art.

The carbon magnetic resonance spectra were recorded deuteriochloroform (EXS. 1,2 and 3) and in deuterium oxide for Example 4. Only signals assigned to carbons of the fortimicin A skeleton are shown and these are described in ppm downfield from tetramethylsilane.

TABLE

| CARBON MAGNETIC RESONANCE SPECTRA | | | | |
| --- | --- | --- | --- | --- |
| | Example 1 | Example 2 | Example 3 | Example 4 |
| $C_1$ | 50.2 | 50.1 | 50.6 | 49.5 |
| $C_2$ | 69.8 | 82.2 | 32.6 | 29.2 |
| $C_3$ | 72.9 | 68.7 | 69.9 | 69.8 |
| $C_4$ | 54.1 | 57.3 | 56.0 | 56.8 |
| $C_5$ | 72.9 | 71.1 | 72.9 | 70.8 |
| $C_6$ | 75.5 | 73.4 | 75.1 | 73.5 |
| $C_1'$ | 97.3 | 97.4 | 97.6 | 95.3 |
| $C_2'$ | 49.9 | 49.9 | 49.9 | 51.7 |
| $C_3'$ | 24.3 | 24.0 | 24.3 | 21.6 |
| $C_4'$ | 27.3 | 27.4 | 27.4 | 26.4 |
| $C_5'$ | 71.7 | 72.0 | 71.8 | 71.3 |
| $C_6'$ | 49.7 | 49.7 | 49.9 | 50.8 |
| $C_7'$ | 18.3 | 18.4 | 18.5 | 15.3 |
| $OCH_3$ | — | — | — | 56.6 |
| $NCH_3$ | — | — | — | 32.0 |
| Glycine | 43.4 | 43.2 | 43.4 | 41.3 |
| | 170.9 | 169.3 | 169.6 | 182.3 |

Assignments have been made by analogy with like carbons in other fortimicin derivatives and from known effects of structures on carbon magnetic resonance chemical shifts. Interchange between assignments to carbons of resonances of similar chemical shifts does not affect the characterization or structural inferences drawn.

Fortimicin A can be produced according to the process of U.S. Pat. No. 3,976,768. The other materials used in the practice of this invention are commercially available or can be synthesized by known literature methods.

What is claimed is:

1. An improved method of producing the antibiotic 2-deoxyfortimicin A comprising the steps of: (a) converting fortimicin A having all primary amino groups blocked to the corresponding per-N-blocked 2-O-thiocarbonylimidazolide; (b) converting said imidazolide derivative to 2-deoxy-tetra-N-benzyloxycarbonylfortimicin A and (c) subjecting said 2-deoxy-N-benzyloxycarbonylfortimicin A to catalytic hydrogenolysis to obtain 2-deoxyfortimicin A.

2. The method of claim 1 wherein said fortimicin A having all primary amino groups blocked is obtained by reacting fortimicin A with the benzyloxycarbonyl ester of N-hydroxysuccinimide to obtain tetra-N-benzyloxycarbonylfortimicin A.

3. The method of claim 2 wherein said tetra-N-benzyloxycarbonylfortimicin A intermediate is reacted with N,N'-thiocarbonyldiimidazole to obtain tetra-N-benzyloxycarbonylfortimicin A-2-O-thiocarbonyl imidazolide.

4. The method of claim 3 wherein said tetra-N-benzyloxycarbonylfortimicin A-2-O-thiocarbonyl imidazolide in dioxane is refluxed in the presence of tri-N-butyl stannane in dioxane to obtain 2-deoxy-tetra-N-benzyloxycarbonylfortimicin A.

5. The method of claim 4 wherein said reaction mixture is refluxed in a nitrogen atmosphere for about three hours.

6. The method of claim 5 wherein said 2-deoxy-tetra-N-benzyloxycarbonylfortimicin A is subjected to hydrogenolysis over 5 percent Pd-C at three atmospheres for about four hours to obtain 2-deoxyfortimicin A.

7. The method of claim 5 wherein said 2-deoxy-tetra-N-benzyloxycarbonylfortimicin A is dissolved in an acid prior to hydrogenolysis to yield a salt of 2-deoxyfortimicin A after said hydrogenolysis.

8. The method of claim 7 wherein said acid is hydrochloric acid and the end product is 2-deoxyfortimicin A hydrochloride.

* * * * *